United States Patent [19]
Marsh

[11] Patent Number: 6,069,131
[45] Date of Patent: May 30, 2000

[54] PRE-OPERATIVE BEVERAGE COMPOSITION AND METHOD OF TREATMENT

[75] Inventor: M. Lou Marsh, Del Mar, Calif.

[73] Assignee: Ohana Medical Concepts, LLC, Del Mar, Calif.

[21] Appl. No.: 09/062,199

[22] Filed: Apr. 17, 1998

[51] Int. Cl.$^7$ .............................. A01N 43/04; A01N 37/00
[52] U.S. Cl. .............................. 514/23; 514/25; 514/557; 514/574
[58] Field of Search ................................ 514/23, 25, 557, 514/574

[56] References Cited

U.S. PATENT DOCUMENTS 5,089,477   2/1992   Fregley et al. ............................ 514/23

OTHER PUBLICATIONS

Douglas, E.,; "Clear, Carbohydrate–Rich Drink Found Safe and Satisfying for Surgical Patients", *Anesthesiology News*, (Mar. 1998).
Dowling, J.; "Nulla Per Os [NPO] After Midnight' Reassessed", *Rhode Island Medicine*, vol. 78, pp. 339–341 (Dec. 1995).
Kinni, M., et al.; "Aspiration Pneumonitis: Predisposing Conditions and Prevention", *J. Oral Maxillofac Surg.*, vol. 44, pp. 378–384 (1986).
Gibbs, C., et al.; "Effectiveness of Bicitra® as a Preoperative Antacid", *Anesthesiology*, vol. 61, pp. 97–99 (1984).
Goresky, G., et al; "Fasting Guidelines For Elective Surgical Patients", *Canadian Journal of Anesthesiology*, vol. 37:5, pp. 493–495 (1990).
Gravenstein, J., et al.; "ASA Meeting Highlights Patient Safety Presentations", *APSF Newsletter*, p. 41, (1996–1997).
Green, C., et al.; "Preoperative Fasting Time: Is the Traditional Policy Changing? Results of a National Survey", *Anesthesiology Analg.*, vol. 83, pp. 123–128, (1996).
Lagerkranser, M., et al.; "Oral Intake of a Carbohydrate Rich Beverage Preoperatively Improves Safety and Well–Being", *Annual Meeting of the American Society of Anesthesiologists*, Abstract #952, (Oct. 1997).
McKinley, A., et al.; "Poster Discussion–Patient Satisfaction, Postoperative Complications", *Anesthesiology*, vol. 83, No. 3A, (Sep. 1995).

Phillips, A., et al.; "Preoperative Drinking Does Not Affect Gastric Contents", *British Journal of Anaesthesia*, vol. 70, pp. 6–9 (1993).
Scarr, M., et al.; "Volume and Acidity of Residual Gastric Fluid after Oral Fluid Ingestion Before Elective Ambulatory Surgery", *CMAJ*, vol. 141, pp. 1151–1154 (Dec. 1989).
Stoelting, R.; "'NPO' and Aspiration: New Perspectives", *48th Annual Refresher Course Lectures and Clinical Update Program*, pp. 1–7, Amer. Soc. of Anesthesiologists, Inc., U.S.A. (1997).
Strunin, L.; "How Long Should Patients Fast Before Surgery? Time for New Guidelines", *British Journal of Anaesthesia*, vol. 70, No. 1, pp. 1–3 (Jan. 1993).
Vincent, R., et al.; "Does 360 ml of Apple Juice Ingested Before Elective Surgery Worsen Gastric Volume and Acidity in Patients Given Acid Aspiration Prophylaxis?", *J. Clin. Anesth.*, vol. 3, pp. 285–289 (Jul./Aug. 1991).

*Primary Examiner*—Rebecca Cook
*Attorney, Agent, or Firm*—Fitch, Even, Tabin & Flannery

[57] ABSTRACT

A specially formulated beverage composition designed to be ingested by a pre-operative patient at least about 2 hours prior to administration of anesthesia is provided herein. The beverage composition is preferably provided in a single-serving volume containing at least about 200 Calories, which Calories are primarily from a non-protein, non-fat source, such as one or more carbohydrates. In a most preferred embodiment, the composition includes about 48 grams maltodextrin, about 6 grams fructose and about 6 grams glucose, in water with enough citric acid to provide a final solution pH of about 4.3. This beverage composition, when ingested during pre-operative fasting, at least about 2 hours prior to administration of anesthesia, encourages compliance with pre-operative fasting requirements; reduces the incidence of symptoms associated with prolonged fasting, such as feelings of hunger and thirst, lightheadedness, irritability and headache; and should reduce the risk of aspiration pneumonia by providing a residual gastric volume and gastric pH within generally accepted ranges. Also, contemplated herein is the method of using this beverage composition to increase compliance with pre-operative fasting guidelines and thereby decrease the risk of aspiration pneumonia in the anesthetized/sedated patient.

11 Claims, No Drawings

PRE-OPERATIVE BEVERAGE COMPOSITION AND METHOD OF TREATMENT

FIELD OF THE INVENTION

The subject matter disclosed and claimed herein relates to a specially formulated beverage composition designed to be administered to a patient, prior to anesthesia and/or sedation, to reduce the risk of aspiration pneumonia at least by increasing compliance with pre-anesthesia/pre-sedation fasting guidelines. In particular, the beverage composition is specially designed to be taken orally, by a patient, within a specified short period of time prior to administration of an anesthesia and/or sedative/analgesic. Further described herein is the method of use of the beverage composition, which method is designed to optimize the benefits of the beverage. Most preferably, the method includes providing a written label of instructions affixed to the beverage container which instructions positively direct the patient's ingestion of the beverage composition and complete fasting thereafter.

BACKGROUND OF THE INVENTION

While conscious and in the erect position, the lower esophageal sphincter (LES) and laryngeal closing reflex of a healthy person prevent regurgitation and aspiration of stomach contents. Administration of anesthesia and/or sedative/analgesic drugs often compromises many natural reflexes, including these reflexes that help protect one's airway from such regurgitation and aspiration. Upon induction of and emergence from anesthesia, as well as intravenous sedation, a patient is at greatest risk for aspiration of gastric contents, particularly because the patient is usually supine. One study has suggested that as many as 20% of patients given general anesthesia for surgery suffer at least some regurgitation and subsequent aspiration. See, Harris, et al., *Can. Anaesth. Soc. J.*, 31:599 (1984).

More than fifty years ago, C. L. Mendelson thoroughly described, for the first time, the symptoms of aspiration of stomach contents into the lungs, now known generally as aspiration pneumonia. Mendelson, C. L., *Am. J. Obstet. Gynecol.* 52:191 (1946). Mendelson's observations, which were made of pregnant women anesthetized during labor, led him to describe two types of aspiration: 1) aspiration of solid gastric material, resulting in blockage of the patient's airway and risk of subsequent suffocation and/or pneumonia; and 2) aspiration of liquid gastric material, resulting in pneumonia and/or other asthma-like symptoms. Aspiration pneumonia, also sometimes referred to as Mendelson's Syndrome, was reproduced experimentally by injecting human acidic vomitus into rabbit tracheas. However, injection of neutralized vomitus caused no such symptoms. It is observations such as these that have led researchers to the conclusion that the acidity of the material aspirated from the stomach is the primary causative factor in aspiration pneumonia. See for example, Kinni, et al., *J. Oral Maxillofac. Surg.* 44:378–384 (1986); and Mendelson, C. L., *Am. J. Obstet. Gynecol.* 52:191 (1946).

While the fully anesthetized patient is at greatest risk of developing aspiration pneumonia, patients subjected to local anesthesia and/or sedative-analgesic medications are also at risk, particularly as the sedation nears the level of hypnosis. To emphasize the importance of the proper monitoring of patients given sedative and/or analgesic medications prior to diagnostic or therapeutic procedures, the American Society of Anesthesiologists (ASA) has eliminated use of the term "conscious sedation" from its practice guidelines and instead refers to "sedation/analgesia". In those guidelines, the ASA recommends that all patients receiving such medications be monitored by a designated individual who is primarily responsible for administration of the sedative and analgesic drugs and for subsequently monitoring the patient's vital signs, which person should not participate in performing the medical procedure. See "The Changing Role of Monitored Anesthesia Care in the Ambulatory Setting," Rêgo, et al. *Anesth Analg.*, 85:1020-36 (1997), referring at page 1021 to "Task Force on Sedation and Analgesia by Non-Anesthesiologists. Practice guidelines for sedation and analgesia by non-anesthesiologists: A report by the American Society of Anesthesiologists Task Force on Sedation and Analgesia by Non-Anesthesiologists," *Anesthesiology,* 84:459–71 (1996). Thus, as used herein, references to the pre-anesthetized patient are intended to refer likewise to those patients scheduled to undergo local anesthesia and/or to be medicated with sedative-analgesic drugs for the purposes of performing a diagnostic and/or therapeutic procedure.

Efforts to eliminate aspiration pneumonia in the anesthetized/sedated patient have focused on both neutralizing the pre-operative stomach contents and reducing the residual gastric volume (RGV) present at induction of anesthesia and/or sedation/analgesia. To this end, guidelines were established for the pre-operative treatment of patients which sought to reduce the risk of aspiration pneumonia by requiring the patient to abstain from all food and all but clear liquids for at least about 12 hours prior to induction and from all liquids for at least eight hours prior to induction. Traditionally, these guidelines have been implemented by a) requiring all patients to fast from midnight the day before their procedure (referred to as nulla per os—nothing by mouth—or the NPO guidelines); b) alkalinization and/or emptying of the stomach just prior to administration of anesthesia/sedation; c) particular vigilance for aspiration during induction of and emergence from anesthesia/ sedation; and d) the use of tracheal intubation, during general anesthesia, to protect the airway and lungs from such regurgitation should it occur. These guidelines, though generally used as much as a century ago, still define the standard of care for the pre-operative patient and have seen little variation in all these years of use.

Until about twenty years ago, it was a relatively simple matter to enforce and monitor the NPO guidelines. Patients typically spent at least the night before surgery in the hospital and thus could be denied food and drink after midnight regardless of whether their surgery was scheduled for 8:00 a.m. the next morning or 4:00 p.m. the next afternoon. Further, these patients could be given intravenous hydration and/or glucose loading solutions to help alleviate the dry mouth, hunger, headaches and nausea frequently associated with fasting, not to mention the irritability those symptoms produce. Thus, compliance with these guidelines was rarely, if ever, a problem.

Today, however, most surgeries are performed on an out-patient basis, partly in response to technological and pharmacological advancements and partly in response to economic pressures, such as those brought about by managed care. By the year 2000, it is estimated that 75% of all surgical procedures, more than 37 million operations per year, will be performed on an out-patient basis. This means that increasingly large numbers of patients will be relied upon to follow the pre-operative, NPO guidelines on their own without medical supervision. Prior to surgery, or other diagnostic or therapeutic procedure requiring anesthesia/ sedation, each patient is asked whether he/she has fasted as instructed. Not only must the medical provider rely on the patient to honestly answer such questions, but, depending upon how the question is posed, the medical provider must also assume that the patient understood what it was he/she was supposed to not do.

While most patients appear to be compliant with the NPO guidelines, many of them complain of headaches, hunger, thirst, irritability, lightheadedness, and similar symptoms associated with fasting for long periods of time. Additionally, a recent survey of patients at an out-patient facility revealed that although patients were given specific guidelines permitting them to ingest clear liquids up to 4 to 6 hours prior to their scheduled time for surgery, the majority of patients opted to fast from midnight, either out of concern about potential aspiration or because of misinterpretation of the instructions. (Informal survey conducted by the inventor at the Frost Street Out-Patient Surgery Center in San Diego, Calif.) At this particular facility, of the nearly 7,000 patients scheduled annually for surgery, 0.41% (28.7 patients) admitted to violating the NPO guidelines. Because these patients failed to follow the prescribed guidelines their surgeries were cancelled or postponed at significant expense to the facility and inconvenience to the patient, the medical providers and the medical staff. The patients' explanations for breaking the fast included forgetfulness, overwhelming thirst or hunger, and simple misunderstandings of the guidelines such as, what was meant by "clear liquids". In addition to the 0.41% of patients at this facility who admitted to violating the NPO guidelines, it must be assumed that some number of patients violated the guidelines but did not admit to doing so and that still other patients failed to follow the guidelines, but did not realize that they had done so. Thus, the total number of patients that either intentionally or unintentionally violated the NPO guidelines would be expected to be much higher than that actually reported.

These experiences of the Frost Street Out-Patient Surgery Center validate two conclusions of a recent larger scale survey concerning the NPO guidelines: (1) that long fasting prior to elective operation is not only uncomfortable for the patient but has detrimental effects, including causing thirst, hunger, irritability, noncompliance and resentment in adult patients, and (2) that confusion exists among physicians as to which "clear liquids" are appropriate prior to surgery, so it is no wonder that patients are not be able to identify the appropriate beverages. See, Green, et al., *Anesth. Anal.* 83:123–8 (1996). Thus, it is clear that compliance with the NPO guidelines presents a serious problem with respect to modern day surgical procedures which are preformed primarily on an outpatient basis.

In addition to issues regarding compliance with the NPO guidelines, the suitability of the guidelines for their purpose has recently been questioned. It has generally been accepted among those of skill in the art that a patient having a residual gastric volume of about 25 ml or more (0.4 ml per kg body weight) and/or a gastric pH of about 2.5 or less, at the time of surgery, is at greatest risk of aspiration pneumonia. It is for this reason that the NPO guidelines have strictly required that patients fast for long periods of time prior to induction in order, presumably, to reduce the RGV and to increase or stabilize the pH of the patients' gastric contents. However, studies have shown that as many as 45% of elective surgery patients, despite having fasted as required, have RGV and/or pH values beyond these critical values and are therefore at significant risk for aspiration pneumonia. Hutchinson, et al., *Anaesth. Intens. Care*, 3:198 (1975); Newson, A. J., *Anaesth. Intens. Care*, 5:214 (1977), and Coobs, et al., *Anesth. Anal.*, 58:183 (1979). Furthermore, recent studies have suggested that prolonged fasting may actually increase gastric volume and acidity (that is, decrease pH), proving to be harmful to the pre-operative patient rather than protective. Scarr, et al. *Can. Med. Assoc. J.* 141:1151–4 (1989); Splinter et al., *Can. J. Anaesth.* 37:36–9 (1990); Sandbar et al., *Anesth.* 71:327-30 (1989); Hutchinson et al., *Can. J. Anaesth.*, 35:12–5 (1988). In fact, for more than four decades it has been known that normal adults and children, ingesting clear liquid volumes of 150 to 300 ml, are apparently able to empty their stomachs in 10 to 20 minutes, making the 8 hour fasting period normally required by the NPO guidelines seem quite extreme. See, Hunt, J. N., *J. of Physiology* (London) 132:267–88 (1956).

Despite the forgoing evidence that adherence to the NPO fasting guidelines does not sufficiently reduce either or both of the defined risks of aspiration pneumonia, most hospitals, clinics, and doctors adhere strictly to the guidelines. Thus, what is needed is a new treatment method that will both address the need to reduce the acidity and volume of the stomach contents of the pre-operative patient and address the need to increase patient compliance with the required pre-operative treatment, whatever it may be. Additionally, it is important to bear in mind that doctors, hospitals, clinics, and managed care administrators are frequently slow to accept changed guidelines with respect to the standard of care for patients; therefore, it is additionally important that any new treatment of the pre-operative patient be acceptable to these medical providers.

SUMMARY OF THE INVENTION

The present invention addresses the above and other needs by providing a specially formulated pre-operative beverage composition which, when ingested during pre-operative fasting at least about 2 hours prior to administration of anesthesia or sedative/analgesia, encourages compliance with pre-operative fasting requirements; reduces the incidence of symptoms associated with prolonged fasting, such as feelings of hunger and thirst, lightheadedness, irritability and headache; and should reduce the risk of aspiration pneumonia by providing a residual gastric volume and gastric pH within the acceptable ranges for administration of anesthesia/sedative. In accordance with one aspect of the present invention, the beverage composition is designed to be readily absorbed, once in the small intestine, thereby delivering energy and fluid to the intracellular space. The beverage further must be well tolerated by the patient without causing GI distress and should be hedonically acceptable with respect to osmolarity, Calories and viscosity. Thus, it is a feature of the present invention to provide a beverage composition that contains at least about 200 Calories; has an osmolarity within the normal physiological range, most preferably about 300 mosm; has a pH of at least about 3.0, and most preferably at least about 4.3; and that provides Calories from a source other than protein or fat. It is a further feature of the present invention that the beverage contain an easily digestible sugar source; have a viscosity about equivalent to that of water and that the composition have a stable shelf life of at least about 6 months. Additionally, of course, it is most preferred that the beverage composition according to the present invention be at least palatable and preferably tasty to the patient.

In accordance with another aspect of the present invention, a method of treatment of patients, prior to induction of anesthesia and/or sedation, is provided. According to this method the patient is instructed, for example by the product label, not to eat any solid foods, nor drink any non-clear liquids, such as milk products, for at least about 8 hours prior to administration of the anesthesia/sedative. Further, and importantly, the patient is positively instructed to ingest the pre-operative beverage composition, according to the present invention, at least about 2 hours prior to anesthesia/sedation and, thereafter, to abstain from all food and beverage. An important feature of this new method is its effect on compliance. Patients are much more likely to comply with instructions to "do something" than to comply with instructions to "not do something;" thus, by providing specific instructions, preferably in the form of written instructions, to patients with respect to ingesting a specific substance, a certain amount of time prior to their medical procedure, with nothing to be a ingested thereafter, patients are much more likely not only to comply with the instructions but to benefit therefrom. Additional aspects and features of the present invention will be apparent to those of skill in the art from reading the following detailed description of the invention provided herein.

DETAILED DESCRIPTION OF THE INVENTION

The following description is of the best mode presently contemplated for carrying out the invention. This description is not to be taken in a limiting sense, but is made merely for the purpose of describing the general principles of the invention. Thus, the scope of the invention should be determined with reference to the claims.

As stated above, it is the generally anesthetized patient that is at most risk of aspiration pneumonia as their natural reflexes are the most compromised. However, use of local anesthesia and/or sedatives and/or a combination of sedative and analgesic medications also places the patient at significant risk for aspiration pneumonia, particularly because individual patients react differently to the various drugs and various doses employed. Furthermore, a small percentage of patients given less than a hypnotic level of anesthesia must be further induced during the procedure, such as when complications arise. It will be appreciated then that the compositions and methods contemplated herein are useful not only for the generally anesthetized patient, but also for those patients undergoing local anesthesia and/or sedation. Thus, as used herein, references to administration of anesthesia or induction of anesthesia or administration of sedatives or induction of sedation are intended to be equivalent and include administration of any drug for the purposes of eliminating pain, reducing consciousness and/or depressing/eliminating conscious and/or unconscious motor activity in the patient during a diagnostic and/or therapeutic procedure.

Additionally, anesthesia and/or sedatives are frequently used for patients undergoing non-surgical procedures, including some diagnostic procedures such as colonoscopy, cardiac catheterization, cardiac pacemaker implantation, gastroscopy and bronchoscopy. Therefore, as used herein, the term "pre-operative" refers to the period of time prior to performance of a diagnostic and/or therapeutic procedure wherein the patient is to be anesthetized and/or sedated. In short, anytime a doctor or other medical provider would require his/her patient to fast for at least about two hours prior to performance of a particular procedure, administration of the beverage composition, as described herein and/or given in accordance with the method described herein, is contemplated.

As stated above, the pre-operative beverage composition of the present invention must achieve certain minimum requirements. For example, once in the small intestine, the beverage must be readily absorbed, thereby delivering energy and fluid to the intracellular space. In addition, the beverage should be well tolerated by the individual patient without causing GI distress. In order to alleviate the hunger associated with prolonged fasting, the beverage composition is most preferably designed to deliver at least about 200 Calories and most preferably about 250 Calories of energy to the patient per single serving (approximately 16 ounces or less). While the requirement for deliverable Calories is high, it is important that the Calories provided be readily digestible by the patient and therefore, generally will not be Calories from either fat or protein. Thus, carbohydrates are a most preferred form of Calorie for the beverage.

It is also important, however, that the beverage composition have an osmolarity within that of the normal physiological range, and most preferably an osmolarity of about 300 mosm. Some carbohydrate sources, such as fructose and glucose, can be used to provide the desirable amount of Calories in a single serving size beverage; however, in these quantities, such carbohydrates result in a beverage having an osmolarity well in excess of the preferred osmolarity of about 300 mosm. Thus, the most preferred carbohydrate sources for use in the present invention are those with a greater polymer content which are also highly digestible and well tolerated, such as maltodextrins.

In a most preferred embodiment, the beverage composition includes a combination of maltodextrin, fructose and/or glucose to provide sufficient Calories while maintaining the desired osmolarity. Three different maltodextrins, M040, M100 and M150, each having a different degree of starch polymer hydrolysis, were considered for use in the most preferred embodiment herein. Through testing of various combinations of maltodextrins and monosaccharides, it was determined that M040 maltodextrin served very well as a primary carbohydrate Calorie source used in combination with fructose and glucose to provide additional Calories, sweetness and a final acceptable osmolarity. In particular, combinations ranging from about 34:8:8 grams to about 50:5:5 grams of maltodextrin:fructose:glucose (200 and 240 Calories, respectively) provided acceptable osmolarities and viscosities. Upon further testing, however, it was determined that the use of M040 maltodextrin ("M040") as the primary carbohydrate source resulted in a beverage that became cloudy upon refrigeration. Thus, it was decided to replace the M040 with M100 maltodextrin ("M100"), thereby preventing the cloudiness observed when the M040 was used.

Medium chain triglycerides were also tested as these oils, although fatty, are handled by the body as carbohydrates. Additionally, triglycerides provide a high level of Calories (8 Calories per gram), with no impact on osmolarity. However, addition of triglycerides to the beverage composition resulted in a cloudy, milky beverage, which might be unappealing to the patient. Additionally, small fat droplets appeared on the surface of the solution suggesting the need for either homogenization of the mixture or the addition of an emulsifier thereto. Thus, triglycerides may be an acceptable alternative Calorie source for the present composition, but are generally disfavored because they can be expected to increase the cost of making the beverage and to be unacceptable to certain patients. Therefore, within the parameters of osmolarity, Calories, viscosity and patient acceptability, the most preferable combination of Calorie-contributing ingredients is about 48 grams M100 maltodextrin, about 6 grams fructose and about 6 grams glucose.

In addition to providing sufficient Calories to thwart the symptoms of prolonged fasting and to encouraging compliance with fasting requirements following ingestion, the beverage composition should be palatable to the patient, so as to encourage compliance with the requirements that the entire beverage be consumed prior to surgery. To that end, numerous possible additives are available and known that may be included in the beverage that will increase palatability without significantly effecting Calories, osmolarity or viscosity of the compostion. For example, flavorings, such as chamomile, licorice, peppermint, ginger, comfrey, citric acid, coffee, tea flavors, raspberry, lemon, and similar flavors may be added to the beverage to enhance its acceptability. In addition to flavoring, it may be desirable to add caffeine to the beverage composition, in particular for those patients that are regular caffeine consumers, as such patients frequently suffer from headaches when deprived of their normal caffeine ingestion. However, some recent studies have suggested that caffeine may have adverse effects on the acidity of stomach contents, and furthermore, Food and Drug Administration (FDA) regulations concerning the addition of caffeine to beverages may be prohibitive. Therefore, the amounts of caffeine used in the presently contemplated beverage composition, if any, should be very carefully monitored.

Numerous other additives may be considered and alternatively are included within the beverage composition. For example, an aspiration prophylaxis may be included in the beverage composition in order to further reduce the risk of acid aspiration during induction of or emergence from anesthesia and/or sedation. Aspiration prophylaxis, such as the class of compounds defined as selective serotonin 5HT3 receptor antagonists, are known to those of skill in the art. Examples of aspiration prophylaxis include such compounds as ranitidine, ondansetron (Zofran, Glaxo Wellcome, Research Triangle Park, N.C.) and metoclopramide. Other histamine antagonists, likewise known to those of skill in the art, may also be included within the beverage, as well as known antacids, such as 0.3 M sodium citrate or Bicitra (Baker Norton Pharmaceuticals, Inc., Miami, Fla.), a urinary alkalinizing drug that contains about 0.3 M sodium citrate.

Additional additives contemplated for use herein include various natural, health-enhancing additives associated with improved healing and well-being, such as vitamins, minerals and herbal and other plant and animal products. In particular, for example, numerous herbal medicines are associated with improved digestive and/or urinary system health, such as ginger (*Zingiber officinale*), plantago seed and husk (*Plantago arenaria*), senna (*Cassia acutifolia* and *augustifolia*), peppermint (Lamiaceae family), chamomile (*Matricaria recutita*), milk thistle (*Silybum marianum*), licorice (*Glycyrrhiza glabra*), goldenrod (*Solidago virgaurea*), bearberry (*Arctostaphylos uva-ursi*), cranberry (*Vaccinium macrocarpon*) and saw palmetto (*Serenoa repens*). Also, various herbal medicines are associated with general health and/or stimulation of the immune system, such as ginseng (*Panax ginseng, quinquefolius*), eleuthero (*Eleutherococcus senticosus*) and echinacea (*Echinacea purpurea*). Vitamins and minerals, such as the B-complex vitamins, vitamins A and C and zinc, as well as others well known to those of skill in the art, are likewise considered useful herein for supplementing the present beverage composition and conferring additional benefits thereto.

It will be appreciated by those of skill in the art that there will be certain contra-indications for use of this pre-operative beverage composition. For example, diabetic patients, pregnant women, trauma victims, the narcotized, and the massively obese patient, as well as any other patient having either a mechanical or neurological basis for retarded gastric emptying should probably not use this beverage. However, for the vast majority of otherwise healthy patients the pre-operative beverage composition contemplated and described herein, may be safely administered with expectations of reducing their risk of acid aspiration during anesthesia/sedation and of improving the general well-being of the patient both pre-and post-surgery.

Thus, the most preferred composition of the pre-operative beverage as contemplated herein includes 320 grams per serving of filtered water, 48 grams per serving of M100 maltodextrin; 6 grams of fructose; 6 grams of glucose; and 0.02 grams of citric acid, resulting in a 355 ml product (approximately 12 ounces) capable of delivering 240 Calories. Further, a preferred embodiment of the beverage composition includes one or more flavorings, such as peppermint, licorice, vanilla, fruit flavors, tea flavoring, coffee flavoring and the like and/or one or more herbal, vitamin and/or mineral supplements as previously described. It will be appreciated by those of skill in the art that various ingredients may be substituted for other ingredients provided herein. For example, the carbohydrate Calorie source may be selected from a number of various carbohydrate Calorie sources well known to those of skill in the art, including without limitation, one or more monosaccharides, such as fructose and glucose (dextrose); disaccharides, such as sucrose, maltose, cellobiose and lactose; polysaccharides, such as various starches (e.g. dextran or dextrin), natural gums and seaweed products such as carrageenan and agar; and their derivatives. It will be appreciated that some polysaccharides, such as cellulose products, are insoluble in water and therefore are not well suited for the purposes of the present invention. Additionally, the monosaccharides and disaccharides are, generally preferred herein, as they contribute a sweet taste to the beverage composition. In selecting a proper carbohydrate source, of primary concern is that it provide an appropriate amount of Calories in a single serving, most preferably of about 16 ounces or less.

The inclusion of citric acid in the most preferred embodiment of the beverage composition, described above, serves a number of purposes, but may be readily substituted by one or more other ingredients, well known to those of skill in the art, which other ingredients may serve one or more of the same purposes. For example, the citric acid lowers to about 4.3 the pH of the most preferred embodiment of the beverage composition which is described above. The citric acid serves to improve the palatability of the product by providing tartness while also eliminating the need for retorting or aseptic packaging of the product due to its acidity. By lowering the pH of the solution to at least about 4.3, simple pasteurization will be sufficient to provide the product with a shelf-life of about six months to a year. Thus, it will be appreciated by those of skill in the art that numerous other acids may be employed to lower the pH of the beverage composition, for example, acetic acid. However, excluding acid from the composition, resulting in a pH above about 4.3, is an acceptable alternative embodiment which does not interfere with the effectiveness of the composition, but will be expected to increase manufacturing costs. Thus, as long as the pH of the final composition is no less than about 3.0 when ingested by the patient, it is acceptable for the purposes herein.

With respect to the palatability of the beverage composition, as contemplated herein, numerous other flavorings may be employed in lieu of or in addition to citric acid. For example, any one or more of chamomile, licorice, peppermint, ginger, comfrey, coffee flavors, tea flavors (such as, raspberry, lemon, orange and the like), fruit flavors, vanilla, cinnamon or other flavoring may be employed to enhance the palatability of the beverage or flavor-enhancing ingredients may be excluded from the composition all together.

It may also be desirable to prepare the composition in a concentrated form. Concentrating the composition may extend its shelf life, as its acidity may thereby increased. Additionally, providing the beverage composition in a concentrated form will allow the patient to select the appropriate amount (within a prescribed range of amounts) and type of water for reconstitution to suit their personal tastes. For example, still or carbonated water may be selected, or the patient may desire to blend the concentrate into crushed ice, providing more texture to the beverage composition. Also, the patient may desire to consume the beverage composition as a small or large volume, again, depending upon their personal preferences. Alternatives along these line will be apparent to those of skill in the art and are likewise contemplated herein.

Further contemplated herein is a method of using the new beverage composition for the treatment of a pre-operative patient. In a most preferred embodiment, the beverage composition is provided to the patient along with instructions for its use, which instructions not only direct the patient to fast from solid foods and all but clear liquids, especially milk products for a specified period of time prior to the scheduled procedure, but also positively instruct the patient to consume the entire beverage composition at a specified time prior to the scheduled procedure. Further, the written instructions command the patient to fast from all food and beverage following consumption of the beverage composition. Appropriate durations of fasting from solids and non-clear liquids are known to those of skill in the art; for example, the patient generally will fast for at least about 8 hours from all solids and non-clear liquids. The appropriate time for ingestion of the beverage composition, prior to anesthesia/sedation, is most preferably selected to be long enough to insure that the patient's stomach has been completely emptied of the beverage at the time of administration of the anesthesia/sedation and to be short enough that the patient experiences the benefits of consuming the beverage, such as alleviation of hunger and thirst pains and avoidance of headaches, lightheadedness and similar symptoms of prolonged fasting. Additionally, the time for ingestion of the beverage should be selected to be close enough to anesthesia/sedative administration to provide a high rate of compliance with the instructions to fast both prior to ingestion and thereafter according to the provided instructions. Most preferably, this time period is at least about 2 hours prior to induction of anesthesia/sedation. Thus, important to the method of using the pre-operative beverage composition contemplated herein, is that the patient be specifically directed, most preferably via a written label affixed to the beverage container, to ingest the beverage at a certain time (or within a certain period of time) prior to administration of the anesthesia/sedative.

While the invention herein disclosed has been described by means of specific embodiments and applications thereof, numerous modifications and variations could be made thereto by those skilled in the art without departing from the scope of the invention as set forth in the claims.

What is claimed is:

1. A method of preparing for induction of anesthesia comprising the steps of:
    a) fasting from solid foods and all non-clear liquids beginning at least about 8 hours prior to said induction and during said at least 8 hour period ingesting only clear liquids without any aspiration prophylaxis or antacid;
    b) ingesting a beverage composition about 2 hours prior to said induction, wherein the beverage composition comprises:
        i) one or more carbohydrates, wherein the total Calories available from the carbohydrates is at least about 200 and wherein the one or more carbohydrates are the sole source of significant Calories;
        ii) an acid, in a quantity sufficient to result in a pH of about 3.0 to about 4.3; and
        iii) water; and
    c) fasting from all food and all liquids following ingestion of the beverage composition.

2. The method according to claim 1 wherein the step of ingesting a beverage composition further comprises ingesting a beverage composition comprising a flavor-enhancing agent.

3. The method according to claim 2 wherein the step of ingesting a beverage composition comprising a flavor-enhancing agent has a flavoring-enhancing agent selected from the group consisting of peppermint, spearmint, cinnamon, fruit flavoring, coffee flavoring, tea flavoring, comfrey, licorice, vanilla and ginger.

4. The method according to claim 1 wherein the step of ingesting a beverage composition comprising one or more carbohydrates has one or more carbohydrates selected from the group consisting of M040 maltodextrin, M100 maltodextrin, M150 maltodextrin, fructose, glucose, maltose, sucrose, cellobiose and lactose.

5. The method according to claim 4 wherein the step of ingesting a beverage composition comprising an acid has an acid selected from the group consisting of citric acid and acetic acid.

6. The method according to claim 5 wherein the step of ingesting a beverage composition comprises ingesting a beverage composition comprising about 48 grams M100 maltodextrin, about 8 grams fructose, about 8 grams glucose, about 0.02 gram citric acid and water.

7. A method of preparing for induction of anesthesia comprising the steps of:
    a) fasting from solid foods and non-clear liquids beginning at least about 8 hours prior to such induction and during said at least 8 hour period ingesting only clear liquids without any aspiration prophylaxis or antacid;
    b) ingesting a single serving beverage composition at least about 2 hours prior to said induction, wherein the beverage composition comprises:
        i) a readily digestible, non-protein Calorie source, wherein the total Calories available from the non-protein Calorie source are about 200 to about 250 and wherein the non-protein Calorie source is the sole source of significant Calories in the beverage and the major portion of said calories is provided by a polysaccharide,
        ii) a water product selected from the group consisting of liquid water and ice; and
        iii) a flavor-enhancing agent selected from the group consisting of an acid, peppermint, spearmint, cinnamon, fruit flavoring, coffee flavoring, tea flavoring, comfrey, licorice, vanilla and ginger; and
    c) fasting from all food and all liquids following ingestion of the beverage composition.

8. The method according to claim 7 wherein the flavor-enhancing agent of the beverage composition ingested in step (b) comprises an acid selected from the group consisting of citric acid and acetic acid and wherein the acid is provided in a quantity sufficient to provide a pH of about 3.0 to about 4.3 to the final beverage composition.

9. The method according to claim 8 wherein the beverage composition ingested in step (b) comprises about 48 grams M100 maltodextrin, about 8 grams fructose, about 8 grams glucose, and about 0.02 gram citric acid in a volume of about 12 fluid ounces.

10. A method of preparing a patient for induction of anesthesia comprising the steps of:
   a) presenting the patient with a labeled beverage container prominently carrying the time of scheduled induction and the time two hours therebefore at which a beverage in said container is to be ingested;
   b) causing the patient to fast from solid foods and all non-clear liquids beginning about 8 hours prior to said induction and to ingest only clear liquids without any aspiration prophylaxis or antacid during the first 6 hours of such 8 hour period;
   c) causing the patient to ingest said beverage composition in said container about 2 hours prior to said scheduled induction, which the beverage composition comprises i) one or more carbohydrates selected from the group consisting of maltodextrin, fructose, glucose, maltose, sucrose, cellobiose and lactose as the sole source of significant calories, with the total Calories available from the carbohydrates being between about 200 and about 250; ii) citric or acetic acid, in a quantity sufficient to result in a pH of about 3.0 to about 4.3; and iii) water; and which composition has a flavor and an osmolarity within the normal physiological range so as to be hedonically acceptable; and
   d) thereafter causing the patient to also refrain from ingesting all liquids and solids following ingestion of said beverage composition, which is aided by said beverage composition ingestion having satisfied the patient's potential hunger and thirst.

11. The method according to claim 10 wherein said beverage composition comprises maltodextrin in an amount to provide the major portion of said calories and has a viscosity about equivalent to water.

* * * * *